United States Patent
Winkler et al.

(10) Patent No.: US 11,826,513 B2
(45) Date of Patent: *Nov. 28, 2023

(54) BREATHING CIRCUIT SYSTEMS AND DEVICES

(71) Applicant: AMBU A/S, Ballerup (DK)

(72) Inventors: Kevin Winkler, Noblesville, IN (US); Yun Siung Tony Yeh, Libertyville, IL (US); Patrick Coleman, McCordsville, IN (US); Charles Rosebrook, Carmel, IN (US); Thomas W. McGrail, Cicero, IN (US); Natasha Reynolds, Noblesville, IN (US); Brian Gerster, Fishers, IN (US); Kleve Heavin, Fishers, IN (US); Jakob Koch, Lyngby (DK)

(73) Assignee: AMBU A/S, Ballerup (DK)

( * ) Notice: Subject to any disclaimer, the term of this patent is extended or adjusted under 35 U.S.C. 154(b) by 398 days.

This patent is subject to a terminal disclaimer.

(21) Appl. No.: 17/087,510

(22) Filed: Nov. 2, 2020

(65) Prior Publication Data
US 2021/0069450 A1 Mar. 11, 2021

Related U.S. Application Data

(63) Continuation of application No. 15/770,455, filed as application No. PCT/US2016/058528 on Oct. 24, 2016, now Pat. No. 10,857,321.
(Continued)

(51) Int. Cl.
*A61M 16/10* (2006.01)
*A61M 16/08* (2006.01)
(Continued)

(52) U.S. Cl.
CPC ...... *A61M 16/107* (2014.02); *A61M 16/0003* (2014.02); *A61M 16/08* (2013.01);
(Continued)

(58) Field of Classification Search
CPC ............ A61M 16/107; A61M 16/0003; A61M 16/08; A61M 16/0816; A61M 16/1045;
(Continued)

(56) References Cited

U.S. PATENT DOCUMENTS

| 3,713,440 A | 1/1973 | Nicholes |
| 3,932,153 A | 1/1976 | Byrns |

(Continued)

FOREIGN PATENT DOCUMENTS

| DE | 3339988 A1 | 5/1985 |
| DE | 60212158 T2 | 4/2007 |

(Continued)

OTHER PUBLICATIONS

Search report issued by the European Patent Office dated May 4, 2021 in corresponding European Application No. 16858457. 1, 6 pages.
(Continued)

*Primary Examiner* — Elliot S Ruddie
(74) *Attorney, Agent, or Firm* — Faegre Drinker Biddle & Reath LLP

(57) ABSTRACT

A filler device includes a distal housing comprising a distal inner port and a distal outer port; a proximal housing comprising a proximal inner port and a proximal outer port, the proximal housing being sealingly affixed to the distal housing to form an inspiratory pathway between the distal inner port and the proximal inner port and to form an expiratory pathway between the distal outer port and the proximal outer port that is fluidly sealed from the inspiratory pathway, the inspiratory pathway being laterally adjacent the
(Continued)

expiratory pathway; and a first filter in the inspiratory pathway or in the expiratory pathway to filter gases flowing through the inspiratory pathway or the expiratory pathway.

23 Claims, 9 Drawing Sheets

Related U.S. Application Data

(60) Provisional application No. 62/300,758, filed on Feb. 26, 2016, provisional application No. 62/245,987, filed on Oct. 24, 2015.

(51) Int. Cl.
*A61M 16/00* (2006.01)
*A61M 16/22* (2006.01)

(52) U.S. Cl.
CPC ...... *A61M 16/0816* (2013.01); *A61M 16/105* (2013.01); *A61M 16/1045* (2013.01); *A61M 16/1055* (2013.01); *A61M 16/1065* (2014.02); *A61M 16/1095* (2014.02); *A61M 16/0051* (2013.01); *A61M 16/0808* (2013.01); *A61M 16/22* (2013.01); *A61M 2016/0027* (2013.01); *A61M 2016/0036* (2013.01); *A61M 2016/1035* (2013.01); *A61M 2205/33* (2013.01); *A61M 2205/3303* (2013.01); *A61M 2205/3368* (2013.01); *A61M 2205/3569* (2013.01); *A61M 2205/3592* (2013.01); *A61M 2205/3653* (2013.01); *A61M 2205/502* (2013.01); *A61M 2205/702* (2013.01); *A61M 2205/705* (2013.01); *A61M 2205/7536* (2013.01); *A61M 2206/11* (2013.01); *A61M 2230/432* (2013.01)

(58) Field of Classification Search
CPC ............ A61M 16/105; A61M 16/1055; A61M 16/1065; A61M 16/1095; A61M 16/0051; A61M 16/0808; A61M 16/22; A61M 2016/0027; A61M 2016/0036; A61M 2016/1035; A61M 2205/33; A61M 2205/3303; A61M 2205/3368; A61M 2205/3569; A61M 2205/3592; A61M 2205/3653; A61M 2205/502; A61M 2205/702; A61M 2205/705; A61M 2205/7536; A61M 2206/18; A61M 2230/432
USPC .......................... 128/205.27, 206.16, 206.17
See application file for complete search history.

(56) References Cited

U.S. PATENT DOCUMENTS

| | | |
|---|---|---|
| 3,954,625 A | 5/1976 | Michalski |
| 4,148,732 A | 4/1979 | Burrow et al. |
| 4,188,946 A | 2/1980 | Rayburn et al. |
| 4,248,219 A | 2/1981 | Moore et al. |
| 4,462,397 A | 7/1984 | Suzuki |
| 4,593,690 A | 6/1986 | Sheridan et al. |
| 4,637,384 A | 1/1987 | Schroeder |
| 4,729,765 A | 3/1988 | Eckels et al. |
| 4,786,298 A | 11/1988 | Billiet et al. |
| 4,846,167 A | 7/1989 | Tibbals |
| 4,966,398 A | 10/1990 | Peterson |
| 4,966,550 A | 10/1990 | Privat |
| 5,195,527 A | 3/1993 | Hicks |
| 5,213,096 A | 5/1993 | Kihlberg et al. |
| 5,716,210 A | 2/1998 | Novak |
| 5,722,391 A | 3/1998 | Rosenkoetter et al. |
| 5,766,468 A | 6/1998 | Brown et al. |
| 5,794,986 A | 8/1998 | Gansel et al. |
| 5,864,938 A | 2/1999 | Gansel et al. |
| 5,901,705 A | 5/1999 | Leagre |
| 6,079,410 A | 6/2000 | Winefordner et al. |
| 6,113,572 A | 9/2000 | Gailey et al. |
| 6,129,082 A | 10/2000 | Leagre |
| 6,209,541 B1 | 4/2001 | Wallace |
| 6,231,085 B1 | 5/2001 | Olson |
| 6,439,231 B1 | 8/2002 | Fukunaga et al. |
| 6,564,799 B2 | 5/2003 | Fukunaga et al. |
| 6,619,287 B2 | 9/2003 | Blackhurst et al. |
| 6,641,177 B1 | 11/2003 | Pinciaro |
| 6,733,556 B1 | 5/2004 | Luigi |
| 6,874,500 B2 | 4/2005 | Fukunaga et al. |
| 6,896,688 B2 | 5/2005 | Richard et al. |
| 6,929,648 B2 | 8/2005 | Richard et al. |
| 7,044,506 B2 | 5/2006 | Dong |
| 7,163,531 B2 | 1/2007 | Seese et al. |
| 7,178,521 B2 | 2/2007 | Burrow et al. |
| 7,191,782 B2 | 3/2007 | Madsen |
| 7,201,168 B2 | 4/2007 | McGrail et al. |
| 7,261,105 B2 | 8/2007 | Fukunaga et al. |
| 7,275,541 B2 | 10/2007 | Fukunaga et al. |
| 7,294,263 B2 | 11/2007 | Johnson et al. |
| 7,418,965 B2 | 9/2008 | Fukunaga et al. |
| 7,527,300 B2 | 5/2009 | Li |
| 7,559,324 B2 | 7/2009 | Smith et al. |
| 7,578,803 B2 | 8/2009 | Rome et al. |
| 7,655,059 B2 | 2/2010 | Wang et al. |
| 7,717,109 B2 | 5/2010 | Fukunaga et al. |
| 7,753,051 B2 | 7/2010 | Burrow et al. |
| 7,862,090 B1 | 1/2011 | Foreman |
| 7,878,553 B2 | 2/2011 | Wicks et al. |
| 7,921,846 B2 | 4/2011 | Marler et al. |
| 8,079,973 B2 | 12/2011 | Herrig et al. |
| 8,297,318 B2 | 10/2012 | Johnson |
| 8,297,661 B2 | 10/2012 | Proulx et al. |
| 8,550,071 B2 | 10/2013 | Striebig et al. |
| 8,596,688 B2 | 12/2013 | Pisula et al. |
| 8,622,058 B2 | 1/2014 | Hacke et al. |
| 8,647,300 B2 | 2/2014 | Kuenzler et al. |
| 8,800,552 B2 | 8/2014 | Burns |
| 8,800,561 B2 | 8/2014 | Orr et al. |
| 8,858,533 B2 | 10/2014 | Downing et al. |
| 8,887,723 B2 | 11/2014 | Ventur et al. |
| 8,967,139 B2 | 3/2015 | Varis et al. |
| 9,108,008 B2 | 8/2015 | Stenzler et al. |
| 9,388,929 B2 | 7/2016 | Lewis et al. |
| 9,523,453 B2 | 12/2016 | Arnold et al. |
| 9,682,224 B2 | 6/2017 | Downing et al. |
| 9,732,891 B2 | 8/2017 | Lewis et al. |
| 9,759,359 B2 | 9/2017 | Papafagos et al. |
| 9,869,413 B2 | 1/2018 | Laakso et al. |
| 9,889,267 B2 | 2/2018 | Wells et al. |
| 10,006,573 B2 | 6/2018 | Frame et al. |
| 10,166,359 B2 | 1/2019 | Breckon |
| 10,213,591 B2 | 2/2019 | Grassl et al. |
| 10,220,198 B2 | 3/2019 | Fuchs et al. |
| 10,823,319 B2 | 11/2020 | Frame et al. |
| 10,857,321 B2 * | 12/2020 | Winkler ............ A61M 16/0816 |
| 11,235,121 B2 | 2/2022 | Kavermann |
| 2001/0047804 A1 | 12/2001 | Fukunaga et al. |
| 2003/0075176 A1 | 4/2003 | Fukunaga et al. |
| 2003/0183232 A1 | 10/2003 | Fukunaga et al. |
| 2005/0022828 A1 | 2/2005 | Fukunaga et al. |
| 2005/0150505 A1 | 7/2005 | Burrow et al. |
| 2005/0178381 A1 | 8/2005 | Daugherty |
| 2005/0188990 A1 | 9/2005 | Fukunaga et al. |
| 2007/0012317 A1 | 1/2007 | Flagler et al. |
| 2010/0152748 A1 | 6/2010 | Penner et al. |
| 2012/0234318 A1 | 9/2012 | Ventur et al. |
| 2015/0040898 A1 | 2/2015 | Breckon |
| 2016/0325070 A1 | 11/2016 | Lu |
| 2017/0007792 A1 | 1/2017 | Nye |
| 2018/0078728 A1 | 3/2018 | Holyoake et al. |
| 2018/0116692 A1 | 5/2018 | Mcginley et al. |
| 2018/0209553 A1 | 7/2018 | Weaver |
| 2018/0280643 A1 | 10/2018 | Nitta et al. |
| 2018/0311457 A1 | 11/2018 | Kavermann |

(56) References Cited

U.S. PATENT DOCUMENTS

| | | |
|---|---|---|
| 2018/0311459 A1 | 11/2018 | Winkler et al. |
| 2019/0022344 A1 | 1/2019 | Lau et al. |
| 2021/0018127 A1 | 1/2021 | Frame et al. |
| 2021/0228289 A1 | 7/2021 | Rohr Daniel et al. |
| 2022/0040618 A1 | 2/2022 | Dundek et al. |
| 2023/0147017 A1 | 5/2023 | Holyoake et al. |

FOREIGN PATENT DOCUMENTS

| | | | |
|---|---|---|---|
| DE | 102011014018 B4 | 10/2016 | |
| EP | 0462412 A2 * | 12/1991 | ............ A61M 16/08 |
| EP | 0462412 A2 | 12/1991 | |
| EP | 0604399 A1 | 6/1994 | |
| EP | 0462412 B1 | 7/1996 | |
| EP | 1277488 A1 | 1/2003 | |
| EP | 1432475 B1 | 6/2006 | |
| EP | 1556111 B1 | 12/2011 | |
| EP | 1706163 B1 | 5/2017 | |
| EP | 3090774 B1 | 8/2017 | |
| EP | 3259006 A1 | 12/2017 | |
| EP | 2823208 B1 | 5/2019 | |
| ES | 2632316 T3 | 9/2017 | |
| FR | 3113604 A1 | 3/2022 | |
| GB | 2558033 B | 1/2020 | |
| WO | 95/31250 A1 | 11/1995 | |
| WO | 2008/041224 A1 | 4/2008 | |
| WO | 2016/157101 A1 | 10/2016 | |
| WO | 2018/106127 A1 | 6/2018 | |
| WO | 2018/145100 A1 | 8/2018 | |
| WO | 2022/036356 A1 | 2/2022 | |

OTHER PUBLICATIONS

Intent to Grant, European Application No. 16 858 457.1, dated Jun. 9, 2022, 40 pages.
Chambers, "Development of both a <lockable and hybrid person— wearable self-contained self-rescuer", 2011, 82 pgs.
Extended European Search report issued by the European Patent Office dated Sep. 3, 2019 in corresponding European Application No. 16858457. 1, 7 pages.
International Preliminary Report on Patentability issued in PCT/US2016/058528 dated May 3, 2018, 9 pages.
International Search Report and Written Opinion issued in PCT/US2016/058528 dated Jan. 25, 2017, 10 pages.
Lutz, Charles C. et al., "Apollo experience report: Development of the extravehicular mobility unit", NASA Technical Note, 1975, 79 pgs.

* cited by examiner

BREATHING CIRCUIT SYSTEMS AND DEVICES

CROSS-REFERENCE TO RELATED APPLICATIONS

The present application is a continuation of U.S. application Ser. No. 15/770,455, filed Apr. 23, 2018, which is a § 371 application of International Application No. PCT/US2016/058528, filed Oct. 24, 2016, which claims the benefit of U.S. Provisional Patent Application No. 62/300,758, filed Feb. 26, 2016, and of U.S. Provisional Patent Application No. 62/245,987, filed Oct. 24, 2015; the aforementioned patent applications are incorporated herein by reference in their entirety.

FIELD OF THE DISCLOSURE

The present disclosure relates generally to medical devices, and more particularly, to breathing circuits and filters structured to circulate inspiratory gases to, and expiratory gases from, a patient.

BACKGROUND

Breathing circuits convey gases from a source of the gases to a patient. The gases generally comprise air and anesthetic drugs. The anesthetic drugs are dispensed by the source of the gases in different amounts before, during, and after a medical procedure. Examples of sources of gases include anaesthesia machines and ventilators, typically found in operating rooms in hospitals. These machines typically recycle exhaled gases and self-calibrate based on the resistance to gas flow presented by the breathing circuit or a portion thereof. Breathing circuits are provided by breathing circuit systems.

Anaesthetic gases intended for the patient may leak to the environment through joints and, if leaks occur, the patient will not receive the desired intervention. Additionally, the leaked anaesthetic gases could be breathed by medical practitioners, with potentially negative outcomes. Furthermore, loss of anaesthetic gases increases treatment costs.

Improved breathing circuits are desirable to overcome the aforementioned problems with current breathing circuits.

The background to the disclosure is described herein, including reference to documents, acts, materials, devices, articles and the like, to explain the context of the present invention. This is not to be taken as an admission or a suggestion that any of the material referred to was published, known or part of the common general knowledge in the art to which the present invention pertains, in the United States or in any other country, as at the priority date of any of the claims.

SUMMARY OF DISCLOSED EMBODIMENTS

Filter devices and breathing circuit devices comprising filter devices are described disclosed. In some embodiments, a filter device includes a distal housing comprising a distal inner port and a distal outer port; a proximal housing comprising a proximal inner port and a proximal outer port, the proximal housing being sealingly affixed to the distal housing to form an inner pathway between the distal inner port and the proximal inner port and to form an expiratory pathway between the distal outer port and the proximal outer port that is fluidly sealed from the inner pathway, the inner pathway being laterally adjacent the expiratory pathway; and a first filter in the inner pathway or in the expiratory pathway to filter gases flowing through the inner pathway or the expiratory pathway.

BRIEF DESCRIPTION OF THE DRAWINGS

The features of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. Although the drawings represent embodiments of the present invention, the drawings are not necessarily to scale and certain features may be exaggerated to better illustrate and explain the embodiments.

DETAILED DESCRIPTION OF DISCLOSED EMBODIMENTS

Figure 1:
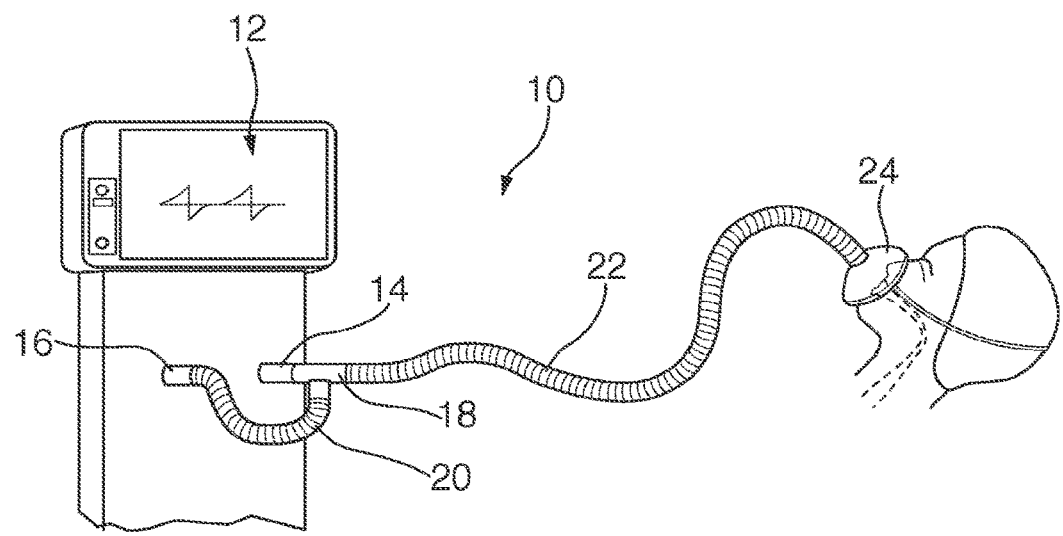
FIGS. 1 and 2 are perspective and schematic illustrations, respectively, of a breathing circuit system forming a breathing circuit.

For the purpose of promoting an understanding of the principles of the invention, reference will now be made to the embodiments illustrated in the drawings and described below. The disclosed embodiments are not intended to be exhaustive or limit the invention to the precise form disclosed in the following detailed description. Rather, the embodiments are chosen and described so that others skilled in the art may utilize their teachings. It will be understood that no limitation of the scope of the invention is thereby intended. The invention includes any alterations and further modifications in the illustrated devices and described methods and further applications of the principles of the invention which would normally occur to one skilled in the art to which the invention relates.

Filter devices and breathing circuit devices comprising filter devices are described below. Ventilators may perform leakage tests and perform self-calibration based on the resistance to gas flow presented by the breathing circuit. The distal end of the breathing circuit may be suitably plugged to permit separate testing of the inspiratory and expiratory tubes. As technology advances, ventilators may be able to detect leakage of smaller amounts of gases, even smaller than what may present a concern from a medical or environmental perspective. Yet if leakage is detected, the breathing circuit may not be used or additional labor may be necessary to determine the cause of the leakage.

Breathing circuits and filter devices are disclosed below that advantageously seal inspiratory and expiratory pathways from each other and from the environment, overcoming the aforementioned problems. Additionally the filter devices may permit size and cost reductions due to their configurations and integration with other components of the breathing circuit.

In some embodiments, a filter device includes a distal housing comprising a distal inner port and a distal outer port; a proximal housing comprising a proximal inner port and a proximal outer port, the proximal housing being sealingly affixed to the distal housing to form an inner pathway between the distal inner port and the proximal inner port and to form an expiratory pathway between the distal outer port and the proximal outer port that is fluidly sealed from the inner pathway, the inner pathway being laterally adjacent the expiratory pathway; and a first filter in the inner pathway or in the expiratory pathway to filter gases flowing through the inner pathway or the expiratory pathway.

As used herein, "unilimb breathing tube" refers to a device having an inner tube inside an outer tube. The inner tube is generally an inspiratory gas tube and the outer tube is generally an expiratory gas tube. Unilimb breathing tubes may also be referred to as coaxial breathing tubes, whether or not the inspiratory and expiratory tubes are concentric. In one embodiment, the inspiratory and expiratory tubes are concentric at their proximal ends and not at their distal ends. In another embodiment, the inspiratory and expiratory tubes are concentric at their proximal ends and also at their distal ends. The unilimb breathing tube is a component of a breathing circuit system formed by the ventilator, the unilimb breathing tube, and a gas delivery device.

As used herein, a "gas delivery device" is a device used to exchange gases between the breathing tube and the patient. Example gas delivery devices include face masks and airway devices including laryngeal tubes, endotracheal tubes, and laryngeal masks. An example face mask is described in commonly owned U.S. Pat. No. 7,753,051, titled "Face Mask Strap System," issued on Jul. 13, 2010, which is incorporated herein by reference. Another example gas delivery device is described in commonly owned U.S. Pat. No. 7,201,168, titled "Non-tracheal Ventilation Tube," issued on Apr. 10, 2007, which is incorporated herein by reference.

An embodiment of a breathing circuit system 10 will now be described with reference to FIGS. 1 and 2. Breathing circuit system 10 forms a breathing circuit shown in FIG. 2. As shown in FIG. 1, breathing circuit system 10 comprises a ventilator 12 having an inspiratory gas outlet port 14 and an expiratory gas inlet port 16. Inspiratory gas outlet port 14 is connected to a manifold 18 which has inspiratory gas and expiratory gas lumens. The inspiratory gas lumen has a proximal port that is offset by about 90 degrees from a proximal port of the expiratory gas lumen. The inspiratory gas lumen and the expiratory gas lumen have coaxial distal ports. As used herein, proximal end refers to the machine end of the breathing circuit and distal end refers to the patient end. A tube 20, which has a single lumen, connects expiratory gas inlet port 16 to the proximal expiratory gas port of manifold 18. The coaxial distal ports of manifold 18 are fluidly coupled to a unilimb breathing tube 22. Unilimb breathing tube 22 includes a distal connector that is connected to a gas delivery device 24. A face mask is shown as an example of a gas delivery device 24. Unilimb breathing tube 22 includes an inner, or inspiratory, tube inside an outer, or expiratory, tube. Both tubes are connected to proximal and distal connectors or to a filter device and the distal connector. Linear expansion of unilimb breathing tube 22 causes both tubes to expand.

Figure 2:
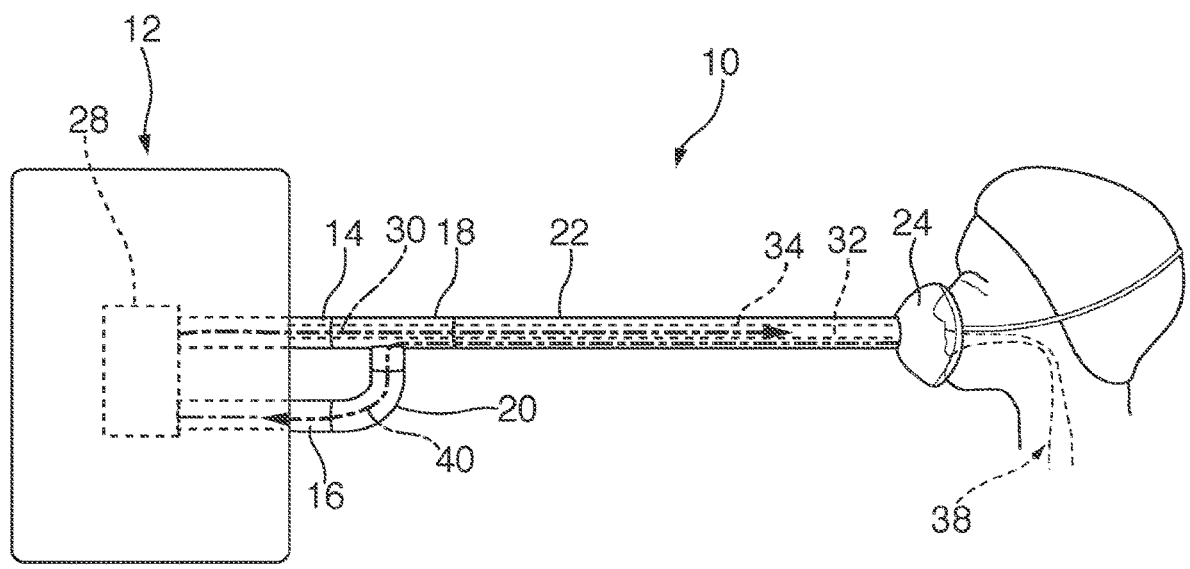

As shown in FIG. 2, a breathing circuit comprises ventilator 12, which may include a carbon dioxide absorber 28 intermediate an inspiratory gas pathway 30 and an expiratory gas pathway 40. Fresh and recycled gases are supplied via inspiratory gas pathway 30 to the lungs 38 of the patient. Expired gases pass through expiratory gas pathway 40 to return to ventilator 12, where they may be scrubbed and recycled. Inspiratory gas pathway 30 includes pathways through inspiratory gas outlet port 14, manifold 18, and an inner tube 32 of unilimb breathing tube 22. Expiratory gas pathway 40 includes pathways through an outer tube 34 of unilimb breathing tube 22, manifold 18, and expiratory gas inlet port 16. Space at the distal end of unilimb breathing tube 22 and within gas delivery device 24, where inspired gases and expired gases are not separated and can mix, is referred to as "deadspace". Ventilators can deliver tidal volumes in pediatric unilimb breathing tubes that may be smaller than the deadspace. Additional components may also be included to connect unilimb breathing tube 22 and gas delivery device 24, such as elbows and swivel connectors. These devices change the orientation of gas delivery device 24 relative to unilimb breathing tube 22.

Generally, breathing tubes include single and dual limb devices. In dual limb devices, the inspiratory tube is not inside the expiratory tube. An advantage of unilimb breathing tubes is that exhaled gases flow around the inspiratory tube warming the gases therein, which aids in maintaining the patient's temperature at a comfortable level. A heat-moisture-exchanger ("HME") can be placed between the unilimb breathing tube and the gas delivery device to warm and moisturize the inhaled gases. The HME may comprise layers of foam and paper impregnated with hygroscopic salts.

Unilimb breathing tubes may comprise drapable and/or collapsible tubing. Drapable tubing comprises corrugations that are not collapsible. Collapsible tubing can, advantageously, be longitudinally collapsed to reduce the length of the coaxial breathing tube for storage and transportation, while enabling longitudinal expansion when the unilimb breathing tube is used. Longitudinal expansion can be controlled to provide a desired length. An example unilimb breathing tube is described in commonly owned U.S. Pat. No. 7,178,521, titled "Adjustable Length Breathing Circuit," issued on Feb. 20, 2007, which is incorporated herein by reference.

A breathing circuit system may include a filter device. The filter device may be located between the unilimb breathing tube and the gas delivery device or between the unilimb breathing tube and the ventilator. If the filter device is positioned between the unilimb breathing tube and the gas delivery device, the unilimb breathing tube may be protected from contamination and, possibly, reused. If the filter device is positioned between the unilimb breathing tube and the ventilator, at least the expiratory tube should not be reused because expired gases may contaminate it. In both instances the filter device may prevent contamination of the ventilator if the filter is interposed in the expiratory path of the breathing circuit. Of course filter devices may be located at both ends of the unilimb breathing tube. However it is preferable to position filter devices at the machine end to reduce clutter near the patient.

Figure 3:
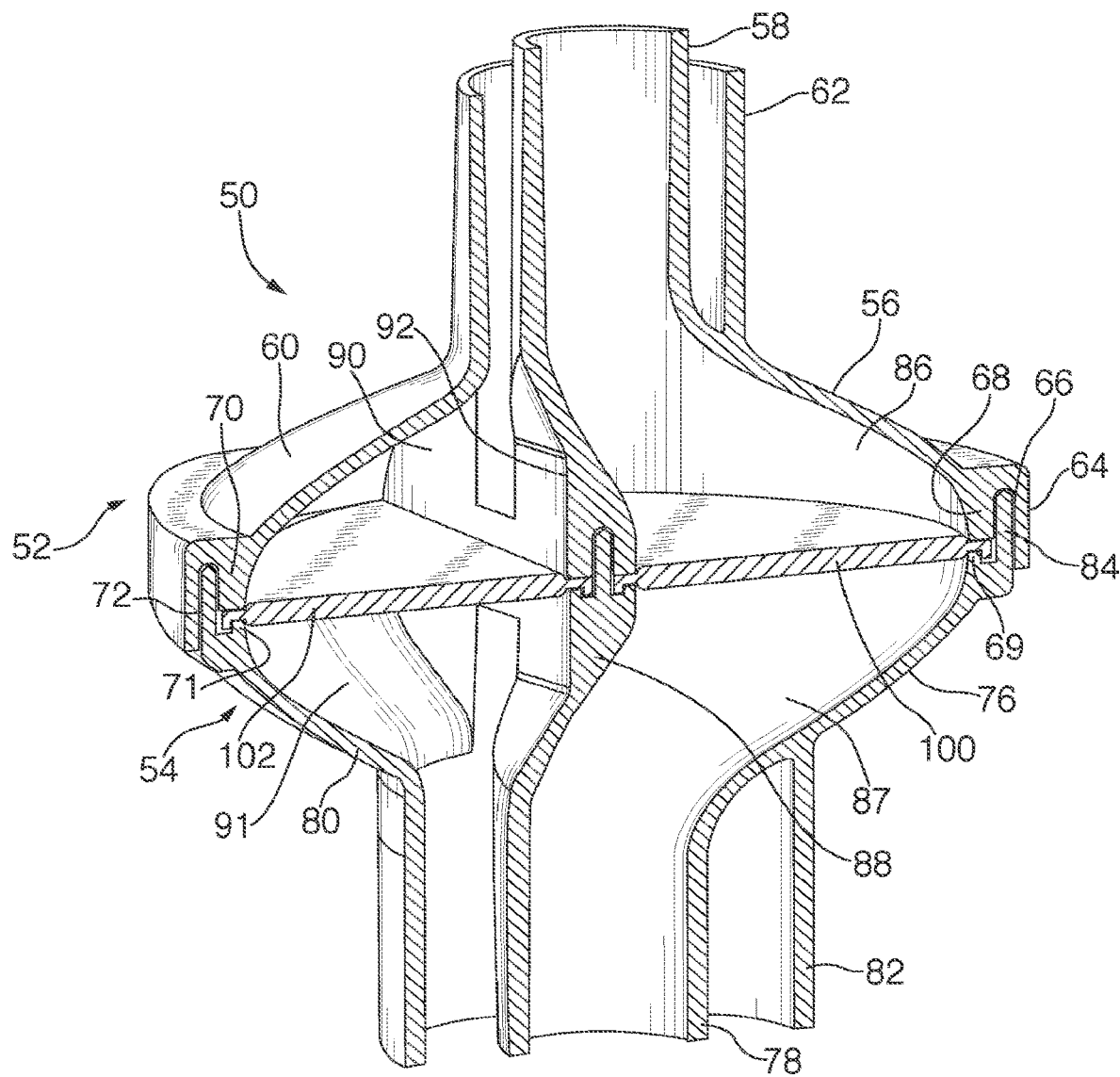
FIG. 3 is a section perspective view illustration of an embodiment of a filter device.
Figure 4:
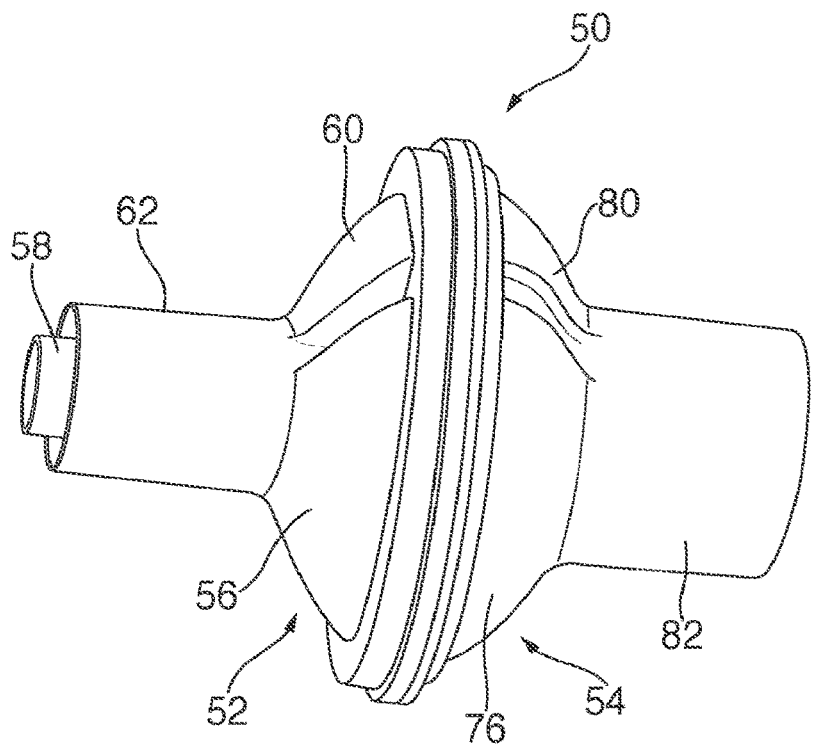
FIG. 4 is a perspective view illustration of the filter device of FIG. 3.
Figure 5:
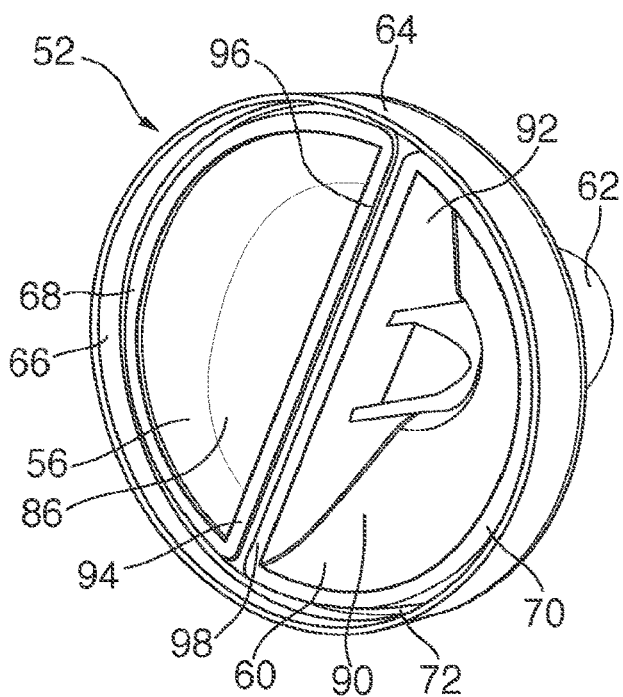
FIG. 5 is a perspective view illustration of a component of the filter device of FIG. 3.

An embodiment of a filter device 50 will now be described with reference to FIGS. 3, 4 and 5. Filter device 50 includes a distal housing 52 coupled to a proximal housing 54. Distal housing 52 includes an inspiratory chamber wall 56, an expiratory chamber wall 60, an inner port 58, and an outer port 62. Distal housing 52 also includes a peripheral wall 64, and a medial wall 92 extending between inspiratory chamber wall 56 and expiratory chamber wall 60. Medial wall 92 ends in walls 94, 98 defining a transverse groove 96 between them (best shown in FIG. 5). Inspiratory chamber wall 56 together with medial wall 92 form an inspiratory chamber 86. Inspiratory chamber wall 56 extends to form an inner wall 68 opposite peripheral wall 64 and forming a groove 66 therebetween. Expiratory chamber wall 60 together with medial wall 92 form an expiratory chamber 90. Expiratory chamber wall 60 extends to form an inner wall 70 opposite peripheral wall 64 and forming a groove 72 therebetween. A filter 100 and a filter 102 are sealingly affixed to filter device 50.

Proximal housing 54 includes an inspiratory chamber wall 76, an expiratory chamber wall 80, an inner port 78, an outer port 82, and a medial wall 88. Inspiratory chamber wall 76 together with medial wall 88 form an inspiratory chamber 87. Expiratory chamber wall 80 together with medial wall 88 form an expiratory chamber 91. Proximal housing 54 also includes a tongue 84, extending from inspiratory chamber wall 76, expiratory chamber wall 80, and medial wall 88, which forms a tongue and groove joint with grooves 66, 72, and 96 when proximal housing 54 is affixed to distal housing 52, thereby sealing inspiratory chambers 86 and 87 and expiratory chambers 90 and 91. Inspiratory chamber wall 76 extends to form an inner wall 69 opposite tongue 84. The edge of filter 100 is affixed between inner wall 68 and inner wall 69. The edge of filter 102 is affixed between inner wall 70 and an inner wall 71 extending from expiratory chamber wall 80, thereby preventing gas flow except through the filters. Substantially all the gases flowing from the ventilator to the patient pass through filter 100 and substantially all the gases flowing from the patient to the ventilator pass through filter 102 when the filter device, the unilimb breathing circuit, and the delivery device are connected properly. When filter device 50 is integrated with unilimb breathing circuit 20, all the gases entering or leaving filter device 50 from/to the ventilator pass through filter 100 or filter 102. When filter device 50 is integrated with unilimb breathing circuit 20, all the gases entering or leaving filter device 50 from/to the ventilator pass through filter 100 or filter 102 and the distal connector of unilimb breathing circuit 20.

Medial walls 88 and 92 divide filter device 50 such that filters 100 and 102 are substantially equal in surface area. In other embodiments, the chamber sizes can be adapted so that filters 100 and 102 are not equal in size. The filters can comprise the same or different filtering media. It may be desirable, for example, to provide a finer inspiratory filter to protect the patient and a less fine filter to protect the ventilator, in which case a larger surface area may be provided for the inspiratory filter to reduce the pressure across it. On the other hand a less fine inspiratory filter may be provided if there is another filter in inspiratory pathway 30. A person of skill in the art would be able to change the volumes of the chambers to achieve a desired pressure differential across the filters based on the chosen filter medium and desired filtration capability. Importantly, by providing only two chambers in each housing, in contrast with prior art filter devices which have four chambers in each housing, laminar flow is improved which reduces resistance to flow. Furthermore, mating of the housings with tongue and groove joints seals the chambers preventing leakage between pathways and to the environment, regardless of pressure.

In some embodiments, filter 102 is omitted and the expiratory chambers are reduced in size to reduce the overall size of filter device 50. In some embodiments, filter 100 is omitted and the inspiratory chambers are reduced in size to reduce the overall size of filter device 50.

Figure 6:
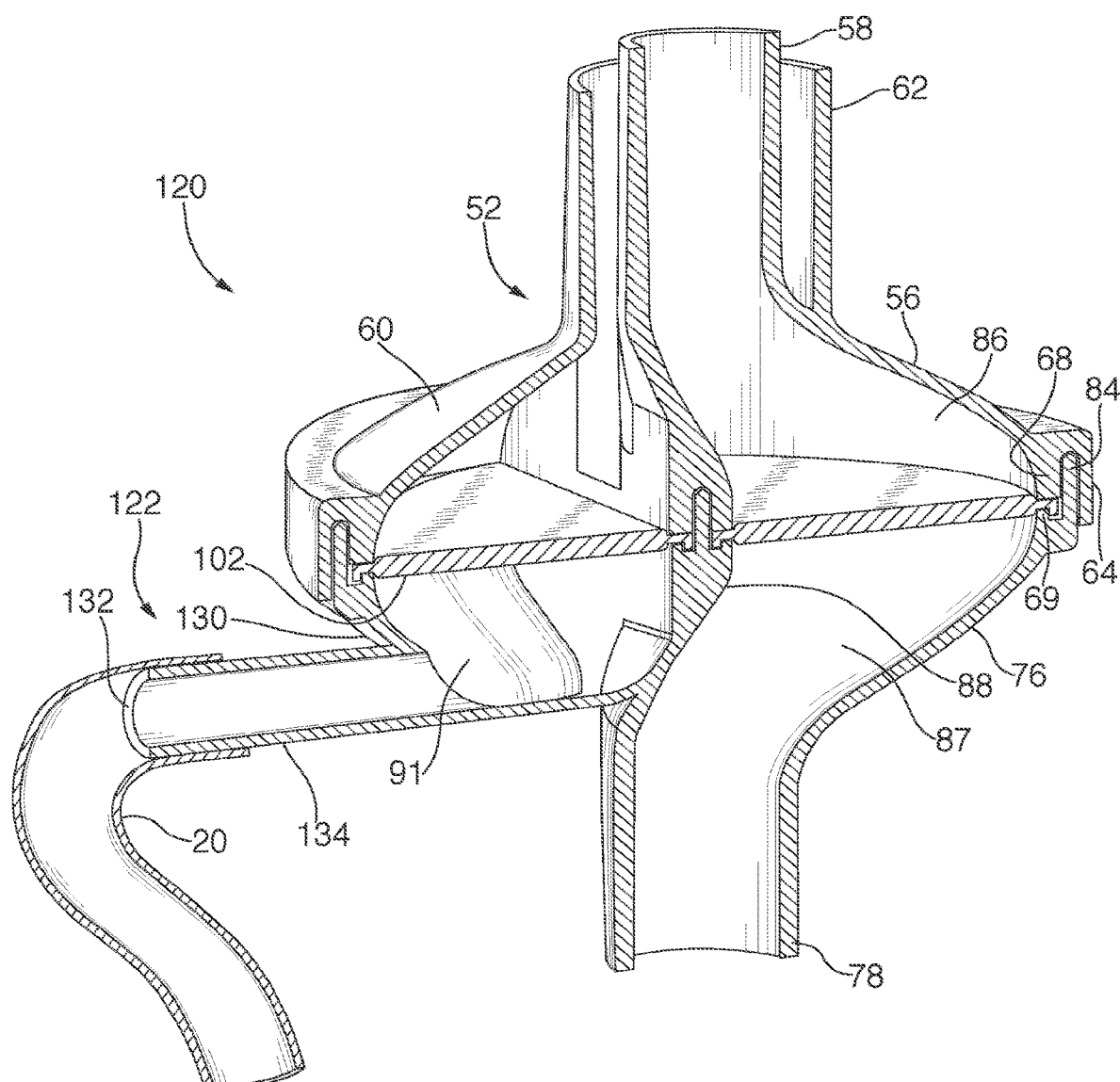
FIG. 6 is a section perspective view illustration of another embodiment of a filter device.

Another embodiment of a filter device, denoted by numeral 120, will now be described with reference to FIG. 6. Filter device 120 is similar to filter device 50, except that proximal housing 54 is modified to incorporate the function of a manifold. Filter device 120 includes distal housing 52 coupled to a proximal housing 122. Proximal housing 122 includes inspiratory chamber wall 76, an expiratory chamber wall 130, inner port 78, and an outer port 132 extending from an expiratory tube 134 connected to expiratory chamber wall 130. Distal ports 58, 62 are co-axial. By using filter device 120 a user avoids the need for a separate manifold, reducing cost and space requirements. In a variation of the present embodiment, filter device 120 is further modified to include the ultrasonic bonding features described with reference to FIGS. 9 and 10.

Figure 7:
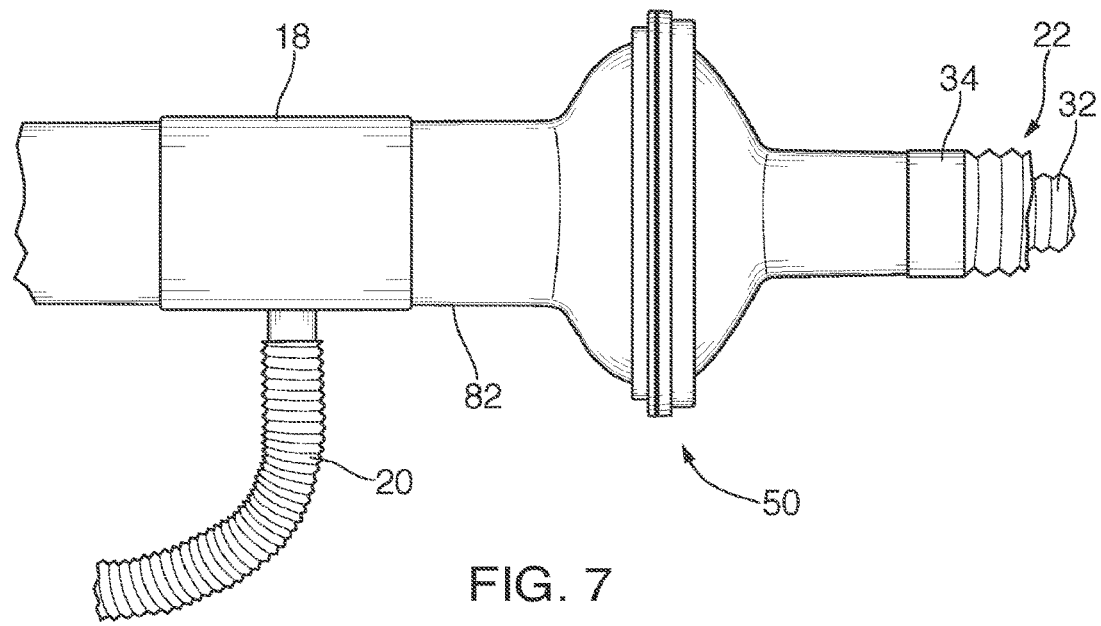
FIG. 7 is an elevation view illustration of an embodiment of a device comprising the filter device of FIG. 3 integrated with a coaxial breathing tube.
Figure 8:
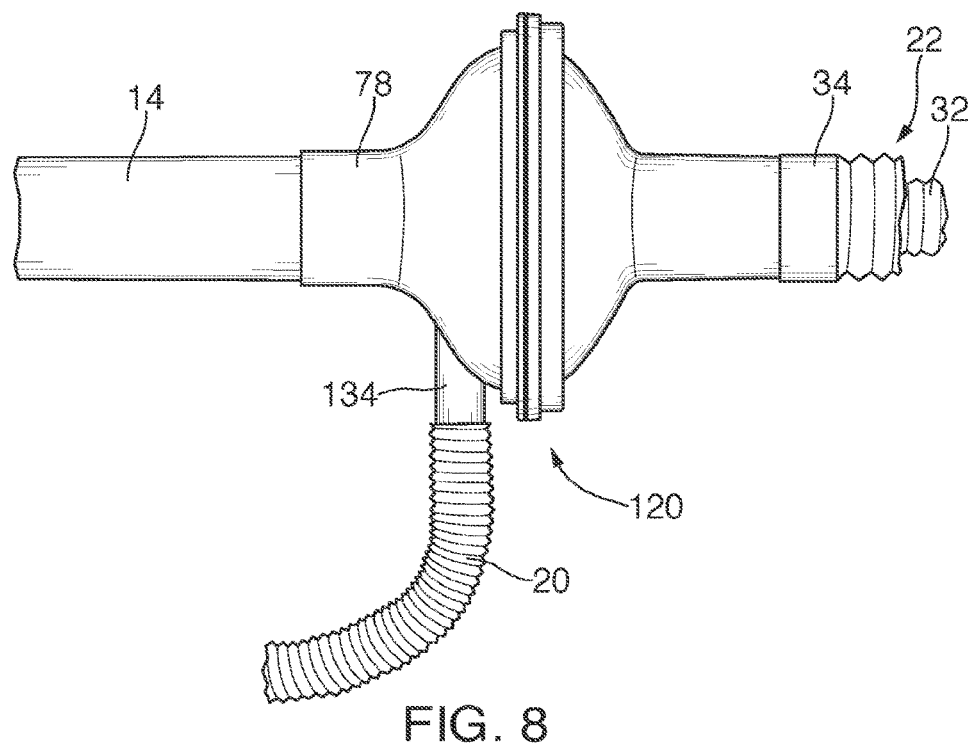
FIG. 8 is an elevation view illustration of an embodiment of a device comprising the filter device of FIG. 6 integrated with a unilimb breathing tube.

In the embodiments described with reference to FIGS. 3 to 6, the filter device is separable from the breathing tube. The breathing tube can be a unilimb tube or a dual limb tube. The filter device is connected to a proximal connector of the breathing tube to form the breathing circuit. FIGS. 7 and 8 illustrate breathing circuit devices incorporating filter devices 50, 120. FIG. 7 shows manifold 18 interposed between ventilator 12 and filter device 50. By contrast, FIG. 8 shows that manifold 18 has been omitted and ventilator 12 is directly connected to filter device 120. Unilimb breathing circuit 22 is sealingly bonded with filter devices 50, 120 further reducing the likelihood of leakage. The bond may be formed by ultrasonic or adhesive bonding, for example. Of course unilimb breathing circuit 22 may be substituted, in some embodiments, with other breathing tubes known in the art, including dual limb tubes and unilimb tubes in which the diameter of the tube is bifurcated by a membrane to form two lumens therein.

Figure 9:
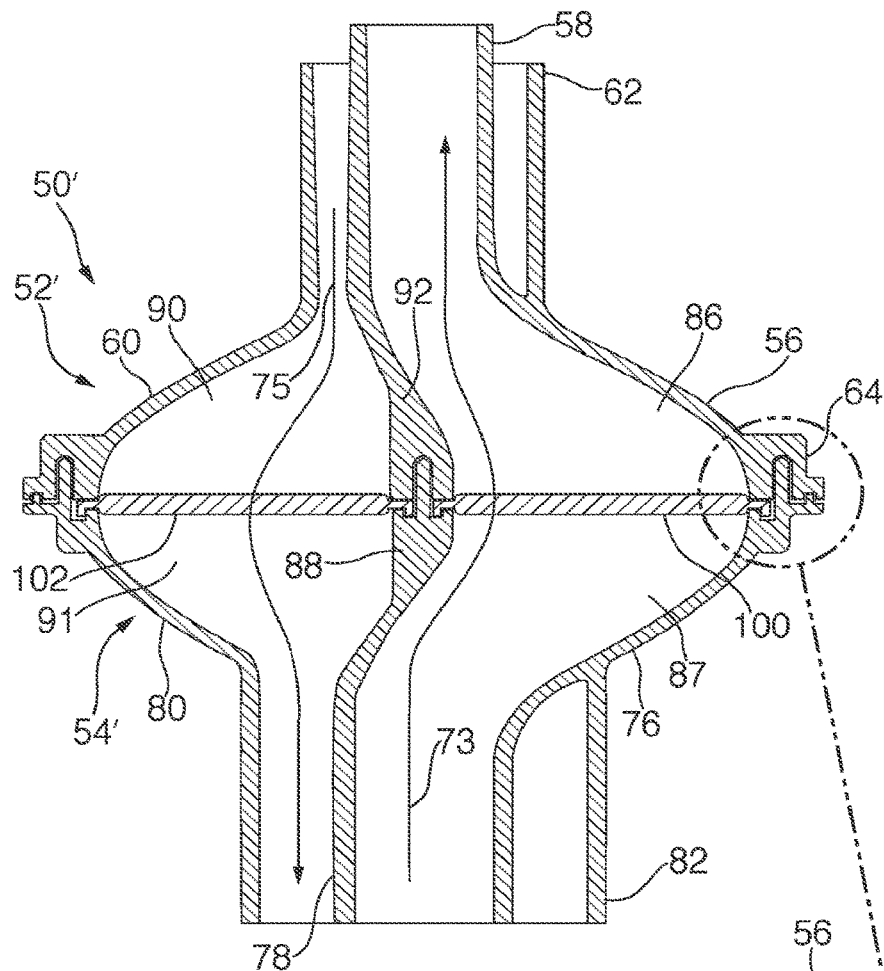
FIG. 9 is a section view illustration of yet another embodiment of a filter device.
Figure 10:
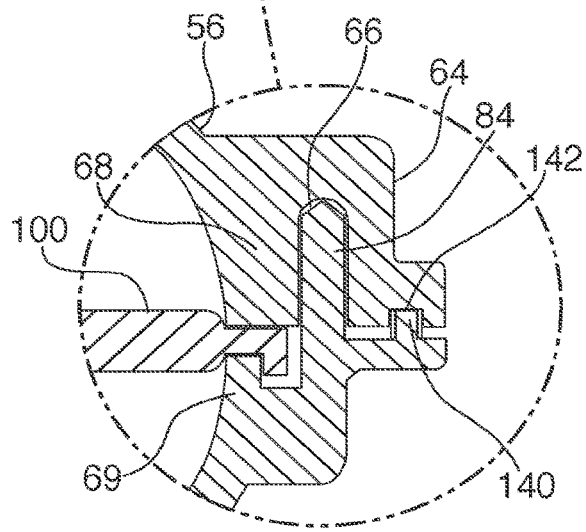
FIG. 10 is an expanded section view illustration of a joint of the filter device of FIG. 9.

FIGS. 9 and 10 illustrate another embodiment of a filter device, denoted by numeral 50'. Filter device 50' includes features which facilitate ultrasonic bonding of a distal housing 52' to a proximal housing 54'. In all other respects distal housing 52 and proximal housing 54 are identical to distal housing 52' and proximal housing 54'. Proximal housing 54' is provided with a collar extending from tongue 66. From the collar a protrusion 140 extends parallel to tongue 84. Protrusion 140 is configured to fit into a groove 142 disposed on distal housing 52'. During construction, after filter device 50' is assembled, ultrasonic energy can be directed to protrusion 140 to ultrasonically bond protrusion 140 and groove 142. In the present embodiment, the tongue and groove joint described with reference with FIG. 50 facilitates assembly by insertion of the tongue into the groove, and creates a press-fit seal, and then the ultrasonic bond provides a fluid seal. The combination of the tongue and groove joint and the fluid seal provides a robust seal between the housings.

In the embodiments described above the tongue is provided in the proximal housing and the groove is provided in the distal housing. In other embodiments the tongue is provided in the distal housing and the groove is provided in the proximal housing.

Figure 11:
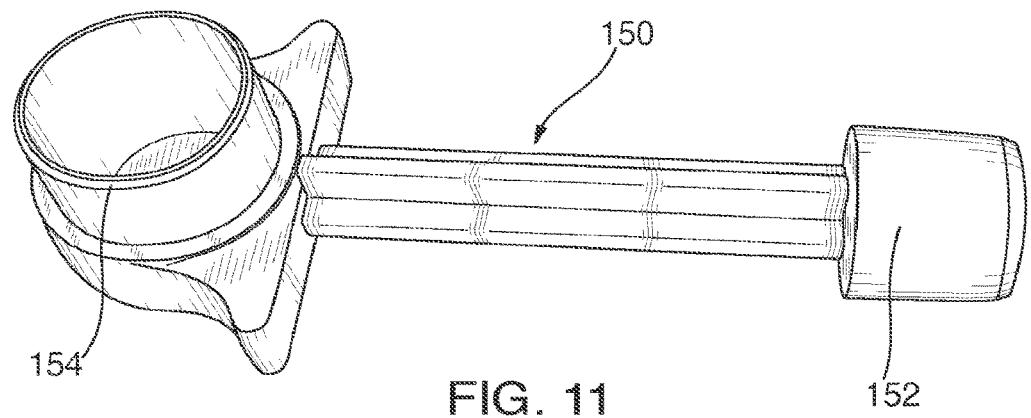
FIG. 11 is a perspective view illustration of an embodiment of a test plug.
Figure 12:
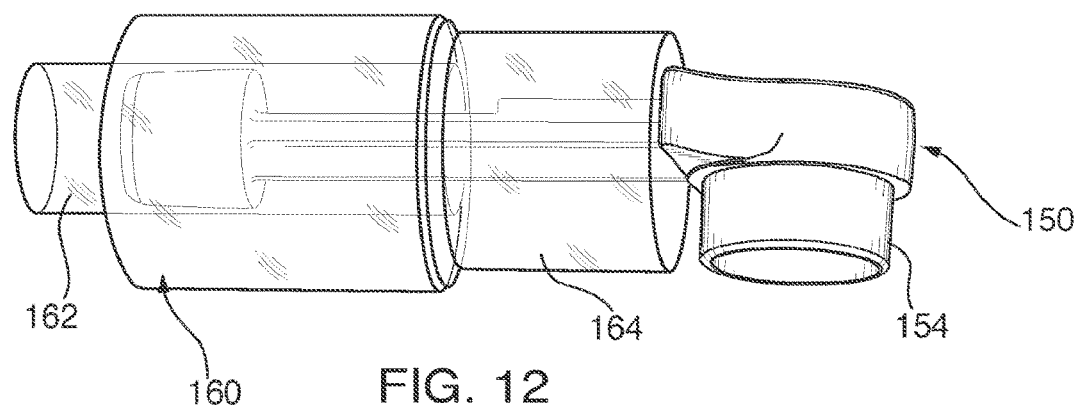
FIG. 12 is a perspective view illustration of the test plug of FIG. 11 blocking an inner port of a unilimb breathing tube.
Figure 13:
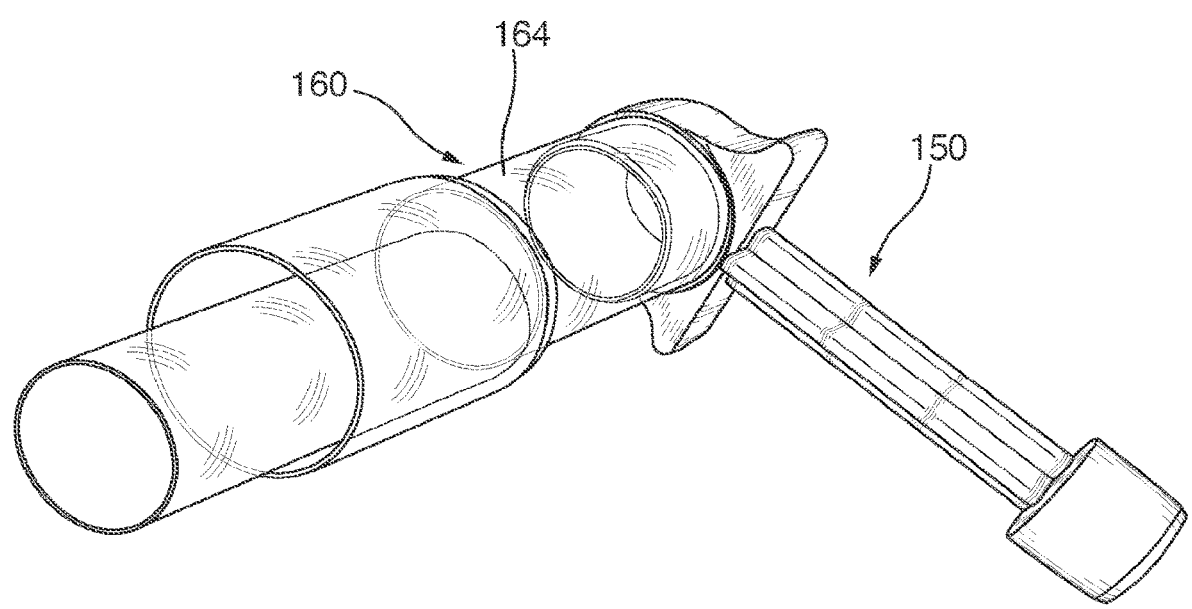
FIG. 13 is a perspective view illustration of the test plug of FIG. 11 blocking an outer port of the unilimb breathing tube.

An embodiment of a test plug 150 will now be described with reference to FIGS. 11, 12, and 13. Test plug 150 comprises an inner port plug 152 and an outer port plug 154. Inner port plug 152 is inserted in an inner port 162 of a distal end connector 160 of a breathing tube to test for leakage in the inspiratory pathway during the leakage test. The breathing tube may comprise breathing tube 22 having distal connector 160. FIG. 12 illustrates inner port plug 152 inserted in inner port 162. FIG. 13 illustrates outer port plug 154 inserted in an outer port 164 of distal end connector 160 to test for leakage in the expiratory pathway. The external circumferences of inner port plug 152 and outer port plug 154 are slightly tapered and configured to press-fit into ports 162, 164 of proximal end connector 160. During the test, the breathing tube is fluidly coupled to the ventilator. The ventilator pressurizes the inspiratory pathway to the test it, with the distal end of the inspiratory pathway plugged by inner port plug 152. The ventilator pressurizes the expiratory pathway to the test it, with the distal end of the expiratory pathway plugged by outer port plug 154. In a similar manner the ventilator may test the filter device.

Figure 14:
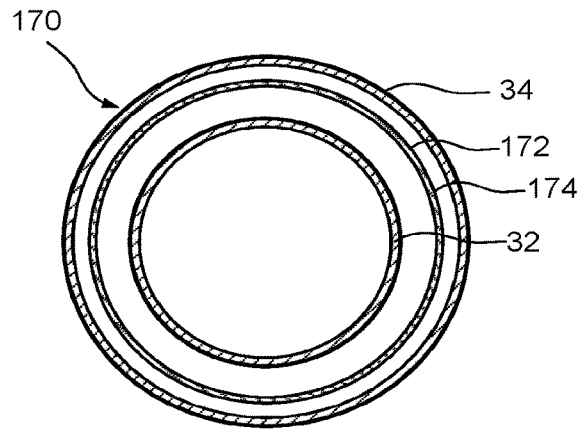
FIGS. 14 to 16 are section elevation view illustrations of embodiments of a unilimb breathing tube.

Tighter seals, lower tidal volumes, and more recycling of expired gases reduce the amount of moisture that may escape or be removed from the unilimb breathing tube. Accordingly, increased amounts of moisture can accumulate. Furthermore, it is desirable to keep moisture from entering the ventilator. Below are described various embodiments, described with reference to FIGS. 14 to 16 comprising absorbent features to trap moisture. These features may be incorporated in the breathing tube, for example breathing tube 22, or in the filter device, for example filter device 50, 50', and 120.

Figure 15:
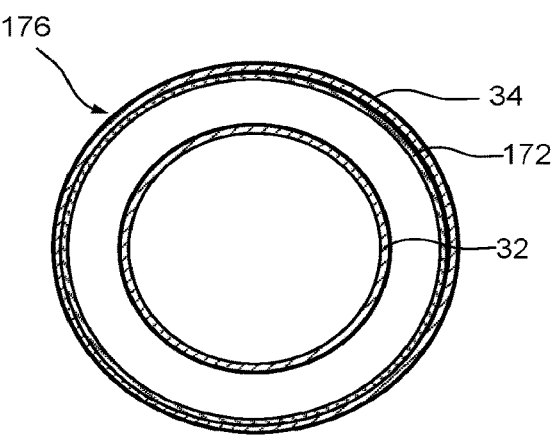
Figure 16:
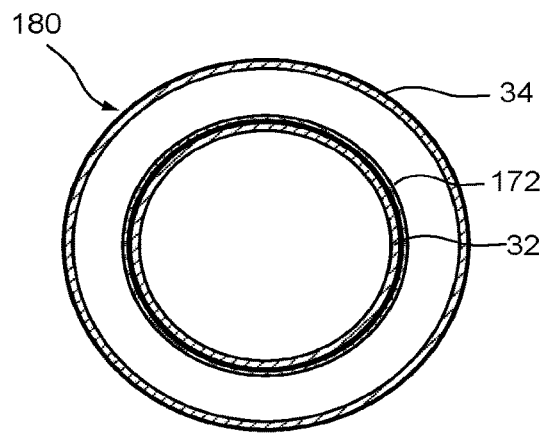

In some embodiments, absorbent material is provided in the expiratory pathway to absorb moisture. In one example the absorbent material comprises superabsorbent gel. In one example, shown in FIG. 14, a tubular insert 174 is disposed between the inner tube 32 and the outer tube 34 of a unilimb breathing tube 170, the tubular insert comprising the absorbent material 172. The absorbent material may also be extruded in a layer of a coextruded expiratory and/or inspiratory tube, or laminated or impregnated instead. FIG. 15 shows absorbent material 172 extruded in an internal layer of external tube 34 of a unilimb breathing tube 176. FIG. 16 shows absorbent material 172 extruded in an external layer of inner tube 32 of a unilimb breathing tube 180. The absorbent material may also be provided in a breathable packet disposed in the expiratory pathway. In one variation, the absorbent material is provided in the filter device described above, for example in the proximal or distal expiratory chambers. Therefore, the filter device accumulates the moisture. The absorbent material may also be incorporated with filter 102.

In some embodiments, the inspiratory tube comprises a moisture permeable membrane. The moisture permeable membrane enables passage of moisture from the expiratory pathway to the inspiratory pathway. The membrane may be located near the proximal end of the unilimb breathing tube. Passage of the moisture to the inspiratory tube reduces moisture in the expiratory tube and also humidifies the inspiratory pathway gases, which is beneficial for the patient. The moisture also transfers heat, thereby heating the inspiratory pathway gases.

An inspiratory tubular extension may be provided which comprises the moisture permeable membrane in order to reduce manufacturing complexity. The extension may be coupled to the inspiratory tube on one end and to the distal inner port of the filter device or the manifold on the other end. In another example, the moisture permeable membrane comprises a monolithic membrane configured to draw moisture via diffusion. An absorbent material may be provided on one side of the monolithic membrane to provide the moisture, which is then diffused to the inspiratory pathway where it is absorbed by the inspiratory pathway gases. Monolithic membranes can comprise, for example, a hydrophilic polyether block amide, which is waterproof while also exhibiting high permeability to moisture vapor. Microporous membranes may also be used. Microporous membranes may comprise, for example, solid particles in a polymer film. Tortuous paths are then formed between the particles by stretching the polymer film. Calcium carbonate is a known solid particle used to make polymeric films. A sulfonated tetrafluoroethylene based fluoropolymer-copolymer membrane may also be used.

In some embodiments, a phase change material is provided. Upon activation of the phase change material, it generates heat to warm the inspiratory pathway gases provided to the patient. Activation may occur, for example, by breaking a package to expose the phase change material to oxygen and generate an exothermic reaction.

In some embodiments, a heating wire is provided to heat the inspiratory tube and thereby heat the inspiratory pathway gases provided to the patient. The heating wire may be disposed in a wall of the inspiratory tube. The heating wire is connected to an electrical energy source, and it heats up due to its electrical resistance.

In some embodiments, a swivel connector is provided. The swivel connector comprises a swivel mechanism which can rotate an element with dual ports, one port being longitudinally aligned with the distal connector of the unilimb breathing tube (e.g. straight) and the other port being offset by 90 degrees. The swivel connector can thus be connected to a face mask, for example, using the offset port, and to another gas delivery device with the straight port. The connector may also comprise two openings, one connected to the straight port and the other to the offset port, and rotating the connector thus connects one or the other port via one or the other openings.

Figure 17:
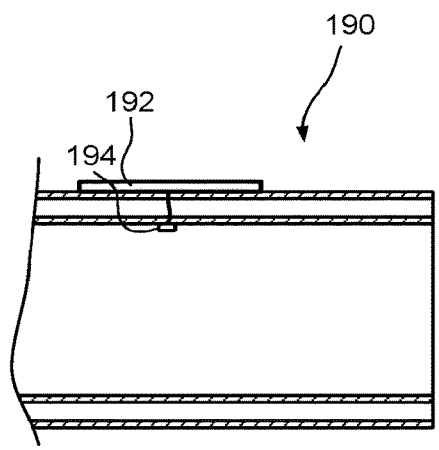
FIG. 17 is a section elevation view illustration of an embodiment of a distal connector of a unilimb breathing tube.

In some embodiments, an integrated circuit 192 (shown in FIG. 17) is provided at or near the distal end of the unilimb breathing tube. Integrated circuit 192 may be connected to distal connector 160, 190 of the unilimb breathing tube of breathing tube 22. A sensing device 194 may be connected to integrated circuit 192. The sensing device may be fluidly coupled to the distal connector, the swivel connector or the gas delivery device to detect a parameter associated with the inspiratory gases. Integrated circuit 192 may include a wireless transmitter configured to transmit a value of the parameter. In one example, the parameter value is transmitted wirelessly to the ventilator, and the ventilator can thus control or adjust the anaesthetic drug volume, the pressure of the inspiratory gases, the temperature of the inspiratory gases, carbon dioxide concentration of expired gases, and any other parameter based on the transmitted parameter value. Advantageously, transmission of parameter values reduces the number of tubes by, for example, eliminating the need to connect a gas sampling tube to the breathing circuit.

Furthermore, measurements obtained near the patient are more beneficial than those obtained remotely, due to time and distance induced variation. The sensor may sense, for example, anaesthetic drug concentration, flow rate, pressure, presence of bacteria, temperature, pressure, movement, etc. Any sensor known in the art may be used.

Integrated circuit 192 may comprise a system-on-a-chip with a processor, analog-to-digital converter, and a wireless transmitter configured to transmit the digital data. The sensor may comprise, for example, an accelerometer or gyroscope to measure motion. The sensor may also measure colors to detect a chemical reaction resulting from the presence of bacteria. A bacteriocidal threshold may be provided to indicate whether the unilimb breathing tube may be reused. If the value is above the threshold, the device must be discarded. The integrated circuit may also provide an alarm signal if the sensed parameter value is outside a safe range. For example, excessive movement may be indicative of patient distress. A discontinuity in flow may be indicative of a disconnection in the breathing circuit or a failure of the ventilator. A wireless receiver may be incorporated in the ventilator or provided in a separate monitoring device, for example in a portable monitoring device usable during transportation of the patient or in the field.

Below are disclosed additional examples of breathing circuit devices.

In an example A, a breathing circuit device comprises an expiratory tube providing an expiratory pathway for expired gases from a patient; an inspiratory tube inside the expiratory tube, the inspiratory tube providing an inspiratory pathway for inspired gases to be provided to the patient; a distal connector connected to the expiratory tube and to the inspiratory tube; a proximal connector connected to the expiratory tube and to the inspiratory tube; and an absorbent material configured to absorb moisture from the expired gases, the absorbent material positioned between the distal connector and the proximal connector.

A breathing circuit device as in example A, wherein the absorbent material comprises a superabsorbent polymer. In one variation, the expiratory tube comprises an external layer and an internal layer, and the absorbent material is supported by the internal layer.

A breathing circuit device as in example A, further comprising a tubular sleeve having a diameter larger than the inspiratory tube and smaller than the expiratory tube, the inspiratory tube passing through the tubular sleeve and comprising the absorbent material.

A breathing circuit device as in example A, wherein the absorbent material is attached to an external surface of the inspiratory tube. In one variation, the absorbent material is laminated to the external surface of the inspiratory tube.

A breathing circuit device as in example A, further comprising a filter device including a distal inner port, a proximal inspiratory port, an inspiratory pathway between the distal inspiratory port and the proximal inspiratory port, a distal expiratory port, a proximal expiratory port, an expiratory pathway between the distal expiratory port and the proximal expiratory port, and at least one filter substrate in at least one of the inspiratory pathway and the expiratory pathway. In one variation, the filter device includes a distal housing having a distal inspiratory chamber fluidly coupled to the distal inspiratory port, and a distal expiratory chamber fluidly coupled to the distal expiratory; and a proximal housing attached to the distal housing and having a proximal inspiratory chamber coupled to the proximal inspiratory port, and a proximal expiratory chamber fluidly coupled to the proximal expiratory port, wherein the distal inspiratory chamber is sealingly attached to the proximal inspiratory chamber forming a sealed inspiratory pathway between the distal inspiratory port and the proximal inspiratory port, and the distal expiratory chamber is sealingly attached to the proximal expiratory chamber forming a sealed expiratory pathway between the distal expiratory port and the proximal expiratory port.

In one variation, the proximal housing comprises a proximal filter connector comprising the proximal inspiratory port and the proximal expiratory port, wherein the proximal filter connector is removably attachable to the distal connector.

In another variation, wherein the distal inspiratory port and the distal expiratory port of the distal housing comprise the distal connector, the proximal inspiratory port is permanently connected to the inspiratory tube, and the proximal expiratory port is permanently connected to the expiratory tube.

In a further variation, the at least one filter substrate comprises a first filter substrate in the inspiratory pathway and a second filter substrate in the expiratory pathway.

In yet another variation, the breathing circuit device further comprises a structural sealing arrangement sealingly connecting the distal inspiratory chamber and the proximal inspiratory chamber, the structural sealing arrangement comprising a wall inserted into a slot, the slot formed in one of the distal housing and the proximal housing, and the wall formed in the other of the distal housing and the proximal housing.

In an example B, a dual-chamber filter device comprises a distal housing having an inspiratory chamber and an expiratory chamber; a proximal housing having an inspiratory chamber and an expiratory chamber; an inspiratory filter between the inspiratory chamber of the distal housing and the inspiratory chamber of the proximal housing; wherein the distal housing and the proximal housing are attached, and wherein an inspiratory chamber structural sealing arrangement sealingly couples the proximal and distal inspiratory chambers to form a sealed inspiratory chamber and an expiratory chamber structural sealing arrangement sealingly couples the distal and proximal expiratory chambers to form a sealed expiratory chamber.

A dual-chamber filter device as in example B, wherein the expiratory chamber structural sealing arrangement comprises a slot surrounding the expiratory chamber and a wall or ledge inserted in the slot to seal the expiratory chamber.

A dual-chamber filter device as in example B, further comprising a distal inspiratory port, a distal expiratory port offset by more than 30 degrees from the distal inspiratory port, a proximal inspiratory port, and a proximal expiratory port, wherein the proximal inspiratory port and the proximal expiratory port are substantially coaxial.

A dual-chamber filter device as in example B, further comprising a distal inspiratory port, a distal expiratory port offset by about 90 degrees from the distal inspiratory port, a proximal inspiratory port, and a proximal expiratory port, wherein the proximal inspiratory port and the proximal expiratory port are substantially coaxial.

In an example C, a breathing tube comprising an inner tube fluidly coupled to the distal inner port; an outer tube fluidly coupled to the distal outer port, wherein the inner tube is positioned inside the outer tube; and a distal connector connecting a distal end of the inner tube to a distal end of the outer tube.

The breathing tube of example C, wherein the inner tube and the outer tube are permanently affixed to the filter device, further comprising a wireless transmitter in the distal connector of the breathing circuit device. In a variation thereof, further comprising a sensor configured to detect a characteristic of a gas flowing through the distal connector, wherein the wireless transmitter is configured to transmit a value of the characteristic of the gas.

The breathing tube of example C, further comprising a wireless transmitter in the distal connector of the breathing circuit device. In a variation thereof, further comprising a sensor configured to detect a characteristic of a gas flowing through the distal connector, wherein the wireless transmitter is configured to transmit a value of the characteristic of the gas.

In an example D, a breathing tube comprising an inner tube fluidly coupled to the distal inner port; an outer tube fluidly coupled to the distal outer port, wherein the inner tube is positioned inside the outer tube; and a distal connector (160) connecting a distal end of the inner tube to a distal end of the outer tube; further comprising an absorbent material positioned between the inner tube and the outer tube.

The breathing tube of example D, wherein the absorbent material comprises a superabsorbent polymer.

The breathing tube of example D, wherein the outer tube comprises an external layer and an internal layer, and the absorbent material is attached to the internal layer.

The breathing tube of example D, wherein the absorbent material is attached to an external surface of the inner tube.

The breathing tube of example D, wherein the absorbent material is laminated to the external surface of the inner tube.

The breathing tube of example D, further comprising a tubular sleeve comprising the absorbent material, wherein the tubular sleeve is positioned intermediate the inner tube and the outer tube, with the inner tube passing through the tubular sleeve.

The breathing tube of example D, wherein the inner tube and the outer tube are permanently affixed to the filter device, further comprising a wireless transmitter in the distal connector of the breathing circuit device. In a variation thereof, further comprising a sensor configured to detect a characteristic of a gas flowing through the distal connector, wherein the wireless transmitter is configured to transmit a value of the characteristic of the gas.

The breathing tube of example D, further comprising a wireless transmitter in the distal connector of the breathing circuit device. In a variation thereof, further comprising a sensor configured to detect a characteristic of a gas flowing through the distal connector, wherein the wireless transmitter is configured to transmit a value of the characteristic of the gas.

While the invention has been described as having exemplary designs, the present disclosure may be further modified within the spirit and scope of this disclosure. This application is therefore intended to cover any variations, uses, or adaptations of the disclosure using its general principles. Furthermore, this application is intended to cover such departures from the present disclosure as come within known or customary practice in the art to which this invention pertains.

What is claimed is:

1. A breathing circuit system, comprising:
   a filter device including:
   a distal housing comprising a first distal chamber wall and a second distal chamber wall, a distal medial wall extending between the first distal chamber wall and the second distal chamber wall, a distal inner port and a distal outer port;
   a proximal housing comprising a first proximal chamber wall and a second proximal chamber wall, a proximal medial wall extending between the first proximal chamber wall and the second proximal chamber wall, a proximal inner tube having a longitudinal axis and a proximal opening forming a proximal inner port, a proximal outer tube having a longitudinal axis and an opening forming a proximal outer port, the longitudinal axis of the proximal outer tube extending laterally relative to the longitudinal axis of the proximal inner tube at an angle of between 60 and 100 degrees, and the proximal housing being affixed to the distal housing to form an inspiratory pathway and an expiratory pathway fluidly sealed from the inspiratory pathway; and
   a first filter in the inspiratory pathway or in the expiratory pathway, to filter gases flowing through the inspiratory pathway or the expiratory pathway.

2. The breathing circuit system of claim 1, the distal housing further comprising a distal inner tube having a distal opening forming the distal inner port; and a distal outer tube defining a lumen and having a distal opening forming the distal outer port, wherein at least a portion of the distal inner tube is positioned in the lumen of the distal outer tube.

3. The breathing circuit system of claim 2, wherein the distal inner tube and the distal outer tube are coaxial.

4. The breathing circuit system of claim 1, wherein the proximal inner tube extends from the first proximal chamber wall and the proximal outer tube extends from the second proximal chamber wall.

5. The breathing circuit system of claim 1, further comprising a test plug including an expiratory pathway plug having a substantially cylindrical wall with an outer surface sized and shaped to plug the expiratory pathway to enable leak-testing of the expiratory pathway, the substantially cylindrical wall having an open end and a closed end opposite the open end.

6. The breathing circuit system of claim 5, wherein test plug comprises an inspiratory pathway plug having an outer surface sized and shaped to plug the inspiratory pathway to enable leak-testing of the inspiratory pathway.

7. The breathing circuit system of claim 6, wherein a diameter of the outer surface of the inspiratory pathway plug tapers longitudinally to enable positioning of the inspiratory pathway plug at least partly into a cylindrical tube of the inspiratory pathway, and wherein a diameter of the outer surface of the expiratory pathway plug tapers longitudinally to enable positioning of the expiratory pathway plug at least partly into a cylindrical tube of the expiratory pathway.

8. The breathing circuit system of claim 6, wherein the test plug comprises a single-piece part including the expiratory pathway plug and the inspiratory pathway plug.

9. The breathing circuit system of claim 6, further comprising
   an inner tube having a proximal end fluidly coupled to the distal inner port, wherein the inspiratory pathway extends through the inner tube;
   an outer tube having a proximal end fluidly coupled to the distal outer port, wherein the expiratory pathway extends through the outer tube; and
   a distal connector having an outer tube connected to a distal end of the outer tube and an inner tube connected to a distal end of the inner tube, the distal connector having a cylindrical gap between the outer tube and the inner tube,
   wherein the outer surface of the expiratory pathway plug is sized and shaped to fit into and fluidly seal the outer tube of the distal connector, and wherein the outer surface of the inspiratory pathway plug is sized and shaped to fit into and fluidly seal the inner tube of the distal connector.

10. The breathing circuit system of claim 9, wherein the substantially cylindrical wall of the expiratory pathway plug is sized and shaped to fit in the gap.

11. The breathing system device of claim 1, wherein the proximal outer tube of the filter device extends further laterally from the proximal housing relative to the proximal medial wall than the second proximal chamber wall.

12. The breathing circuit system of claim 1, further comprising a tongue and groove joint comprising a groove formed in the distal housing or the proximal housing and a tongue formed in the other of the distal housing or the proximal housing, the tongue and groove joint forming a first fluid seal between the expiratory pathway and the inspiratory pathway from each other and from the external environment.

13. The breathing circuit system of claim 12, further comprising a circumferential protrusion formed in the distal housing or the proximal housing and a circumferential groove formed in the other of the distal housing or the proximal housing, the circumferential protrusion configured to fit in the circumferential groove during assembly.

14. The breathing circuit system of claim 13, wherein the circumferential protrusion and the circumferential groove are disposed outwardly of the tongue and groove joint and form a second fluid seal.

15. A method of testing a breathing circuit, comprising:
providing a breathing circuit including a filter device comprising a distal housing comprising a first distal chamber wall and a second distal chamber wall, a distal medial wall extending between the first distal chamber wall and the second distal chamber wall, a distal inner port and a distal outer port; a proximal housing comprising a first proximal chamber wall and a second proximal chamber wall, a proximal medial wall extending between the first proximal chamber wall and the second proximal chamber wall, a proximal inner tube having a longitudinal axis and a proximal opening forming a proximal inner port, a proximal outer tube having a longitudinal axis and an opening forming a proximal outer port, and the proximal housing being affixed to the distal housing to form an inspiratory pathway and an expiratory pathway fluidly sealed from the inspiratory pathway; and a first filter in the inspiratory pathway or in the expiratory pathway, to filter gases flowing through the inspiratory pathway or the expiratory pathway;
fluidly sealing the inspiratory pathway with an inspiratory pathway plug of a test plug;
pressurizing the inspiratory pathway;
monitoring a pressure in the pressurized inspiratory pathway to detect a leak;
fluidly sealing the expiratory pathway with an expiratory pathway plug of the test plug;
pressurizing the expiratory pathway; and
monitoring a pressure in the pressurized expiratory pathway to detect a leak.

16. The method of claim 15, wherein pressurizing of the inspiratory pathway occurs prior to or after pressurizing of the expiratory pathway.

17. The method of claim 15, wherein, wherein the longitudinal axis of the proximal outer tube of the filter device extends laterally relative to the longitudinal axis of the proximal inner tube at an angle of between 60 and 100 degrees.

18. The method of claim 15, wherein the inspiratory pathway plug and the expiratory pathway plug are positioned at opposite ends of the test plug.

19. The method of claim 15, wherein fluidly sealing the inspiratory pathway comprises press-fitting the inspiratory pathway plug into an inner tube of a distal connector of a unilimb circuit.

20. The method of claim 19, wherein fluidly sealing the expiratory pathway comprises press-fitting the expiratory pathway plug into an outer tube of the distal connector of the unilimb circuit.

21. A test plug for testing a breathing circuit system, comprising:
an expiratory pathway plug having a substantially cylindrical wall with an outer surface sized and shaped to plug an expiratory pathway and thereby enable leak-testing of the expiratory pathway, the substantially cylindrical wall having an open end and a closed end opposite the open end; and
an inspiratory pathway plug having an outer surface sized and shaped to plug an inspiratory pathway and thereby enable leak-testing of the inspiratory pathway.

22. The test plug of claim 21, wherein the substantially cylindrical wall has a cylindrical inner surface with a diameter larger than the outer surface of the inspiratory pathway plug.

23. The apparatus of claim 22, wherein the inspiratory pathway plug and the expiratory pathway plug extend from opposite ends of the test plug.

* * * * *